(12) United States Patent
Onimus et al.

(10) Patent No.: US 7,182,932 B2
(45) Date of Patent: Feb. 27, 2007

(54) CATALYST PREPARATION

(75) Inventors: Wilson H. Onimus, Holmes, PA (US); Bernard Cooker, Malvern, PA (US); Edrick Morales, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 446 days.

(21) Appl. No.: 10/769,359

(22) Filed: Jan. 30, 2004

(65) Prior Publication Data

US 2005/0171364 A1 Aug. 4, 2005

(51) Int. Cl.
*B01J 29/89* (2006.01)
*C07D 301/04* (2006.01)
*C07D 301/12* (2006.01)

(52) U.S. Cl. .................. 423/716; 423/326; 502/242; 549/531; 549/532

(58) Field of Classification Search ............... 423/716, 423/326; 502/242, 66, 74, 60; 549/531, 549/532
See application file for complete search history.

(56) References Cited

U.S. PATENT DOCUMENTS

| 4,824,976 | A |   | 4/1989  | Clerici et al. |
|-----------|---|---|---------|----------------|
| 4,833,260 | A |   | 5/1989  | Neri et al. |
| 4,954,653 | A | * | 9/1990  | Bellussi et al. .............. 564/223 |
| 6,005,123 | A |   | 12/1999 | Dessau et al. |
| 6,008,388 | A |   | 12/1999 | Dessau et al. |
| 6,106,803 | A | * | 8/2000  | Hasenzahl et al. .......... 423/705 |
| 6,281,369 | B1 |   | 8/2001  | Cooker et al. |
| 6,441,204 | B1 |   | 8/2002  | Grey |
| 6,498,259 | B1 |   | 12/2002 | Grey et al. |
| 6,551,546 | B1 |   | 4/2003  | Grosch et al. |
| 6,555,493 | B2 |   | 4/2003  | Cooker et al. |
| 6,805,851 | B1 | * | 10/2004 | Muller et al. ................ 423/705 |
| 6,849,570 | B2 | * | 2/2005  | Hasenzahl et al. .......... 502/242 |
| 6,960,671 | B2 | * | 11/2005 | Cooker et al. ............... 549/533 |
| 2003/0083190 | A1 | * | 5/2003 | Carati et al. .................... 502/64 |
| 2003/0130116 | A1 | * | 7/2003 | Hasenzahl et al. .......... 502/242 |
| 2005/0282699 | A1 | * | 12/2005 | Grey ........................... 502/66 |

FOREIGN PATENT DOCUMENTS

JP  4-352771  12/1992

* cited by examiner

*Primary Examiner*—David Sample
(74) *Attorney, Agent, or Firm*—William C. Long

(57) ABSTRACT

A TS-1 catalyst suitable for the production of oxirane compounds is prepared by subjecting conventionally formed TS-1 to a size reduction treatment such as milling such that the average particle size weighted by volume of the TS-1 is reduced to less than 10 microns in diameter and the size reduced TS-1 is spray dried.

8 Claims, No Drawings

CATALYST PREPARATION

FIELD OF THE INVENTION

The present invention relates to catalyst preparation, especially to the spray drying of TS-1, optionally with binder, the particular improvement being the reduction in median particle size of the solid particles in the spray dryer feed weighted by volume to below 10 microns, preferably to below 5 microns prior to spray drying.

DESCRIPTION OF THE PRIOR ART

In certain chemical processes such as the production of propylene oxide, an important catalyst which is used is TS-1, i.e. titanium silicalite. See, for example, U.S. Pat. No. 6,441,204 B1, U.S. Pat. No. 6,498,259 B1, U.S. Pat. No. 6,555,493 B2 and the like.

Although procedures for spray drying TS-1 have been taught in the prior art, e.g. U.S. Pat. No. 4,824,976 and U.S. Pat. No. 6,551,546 B1, including a step of first milling the TS-1 to a size below 200 microns before drying, it has now been found that size reduction of the TS-1 to a size which is very much smaller than the 200 micron upper limit of the art before spray drying results in a catalyst which is remarkably improved for use in propylene oxide production.

BRIEF DESCRIPTION OF THE INVENTION

In accordance with the present invention, TS-1 crystals as conventionally produced as well as any accompanying binder are subjected to a size reduction step wherein the solid particles are reduced in size to a median particle size below 10 microns weighted by volume and preferably below 5 microns before being spray dried.

DETAILED DESCRIPTION

The titanium silicalite which is used in practice of the invention is prepared by well known procedures. A comprehensive description of the titanium silicalite preparation is given in U.S. Pat. No. 4,833,260 the disclosure of which is incorporated herein by reference.

The particulate TS-1 so produced is useful as a catalyst for the reaction of hydrogen peroxide and an olefin to produce an oxirane product. In addition, the TS-1 can be impregnated with a noble metal, such as palladium, and the impregnated product used to catalyze the reaction of oxygen, hydrogen and olefin to produce an oxirane product. See, for example, Japan Kokai No. 4-352771, U.S. Pat. No. 6,281,369, U.S. Pat. No. 6,005,123, U.S. Pat. No. 6,008,388 and the like the disclosures of which are incorporated herein by reference.

The TS-1 or titanium silicalite catalyst is generally used as a slurry or suspension of solid catalyst particles in an appropriate liquid during the actual reaction to produce oxirane product. Frequently it is advantageous to improve the physical characteristics of the catalyst particles by providing a binder such as silica or alumina in association with the TS-1.

Spray drying techniques have been employed in prior procedures in order to prepare TS-1 catalyst particles. See U.S. Pat. No. 4,824,976 and U.S. Pat. No. 6,551,546 which are referred to above.

It has now been found that before spray drying, TS-1 as normally produced and also in admixtures with binder, is comprised to a substantial extent of hard lumps which may be 10 to 15 microns or considerably more in median diameter weighted by volume. It has further been found that such relatively large lumps gives significant inhomogeniety to the catalyst product resulting from the spray drying of such lump containing TS-1, causing mechanical weakness of the catalyst product.

In accordance with the present invention, TS-1, per se or in admixture with binder, is first subjected to a size reduction step such as milling to reduce the median particle diameter weighted by volume to below 10 microns and preferably below 5 microns prior to spray drying. The size reduced material is then spray dried to form a uniform powder product having superior utility as catalyst for the conversion of olefins to oxirane derivatives.

The pre-spray drying size reduction carried out in accordance with the invention can comprise ball milling, jet milling or any of the previously known methods for size reduction, or combinations thereof. The size reduction is done without the addition of water in accordance with known pneumatic techniques.

What is essential is that the median particle diameter weighted by volume of the TS-1 or TS-1 and binder mixture be reduced to below 10 microns, preferably below 5 microns before spray drying.

The size reduced TS-1 is dispersed in an aqueous carrier and spray dried in accordance with known techniques. It is generally advantageous to conduct the spray drying under conditions appropriate to produce a product having about 30 to 40 micron median volume weighted diameter for use in subsequent epoxidation reactions. Among the spray drying variables which can be adjusted to produce the desired product are feed slurry droplet size and feed rate to the dryer as well as drying air temperature and rate of evaporation.

We have found experimentally that the faster the feed rate, the larger the drops and the larger the resulting particles. This arises from the higher feed rate thickening the layer of spinning slurry on the disc, which thickens the lamellar and drops in the atomization process. Also, the faster the feed rate, the greater the rate of interparticle and interdrop and drop/particle collision; the drop and particle density in the dryer rises with feed rate, making inter-particle collisions more likely. We have found that larger particles are intrinsically weaker by virtue of size alone and the lower surface area to volume ratio causes the drying particles to blow up through the water vapor efflux blowing a hole in the surface. This causes poor morphology and weak particles. These considerations limit the slurry feed rate to 0.15 to 0.20 gpm on an approximately 6 inch diameter atomizing wheel. Higher feed rates, up to 0.8 gpm have been used, with atrocious morphology and very poor strength.

Good products have been made for example, at 700–800° F. air feed temperature. Overall, the higher the feed air temperature, the hotter the water evaporation regime in the dryer and the faster the evaporation rate. However, if the evaporation is too fast, the particles are internally stressed by the pressure of the water vapor, causing cracking, holes being blown in the side or bodily disintegration of the particle to fragments like popcorn. Thus an air feed temperature below 850° F., preferably 800° F. or even better 700° F. is required.

TS-1 as used herein is formed in conventional fashion as described, for example, in U.S. Pat. No. 4,833,260. According to the present invention, the TS-1, optionally in admixture with a binder such as silica, is subjected to a size reduction procedure such as milling to reduce the median particle size weighted by volume to below 10 microns diameter, and preferably to below 5 microns diameter and thereafter the size reduced particles are spray dried to form a product useful, for example, as catalyst for the production of oxiranes such as propylene oxide.

The following example is provided as illustrative of the invention.

EXAMPLE 1

400 gm of 40 wt % aqueous tetrapropylammonium hydroxide (TPAOH) is diluted to 25 wt % with water and cooled in an ice bath. To 364 gm of chilled stirred tetraethylortho silicate (TEOS) is slowly added 8 gm of chilled tetraethylorthotitanate (TEOT) with continued mixing. The 25 wt % TPAOH solution is slowly added to the TEOS/TEOT mixture and the resulting mixture is returned to room temperature. The mixture is then placed in a metal autoclave, and the temperature is slowly ramped to 170° C. and held at 170° C. for 3 days with the formation of crystals of TS-1. The resulting slurry is recovered from the autoclave and the TS-1 crystals separated by filtration and washed with water. The TS-1 crystals are dried at 110° C. and calcined at 550° C.

The calcined TS-1 has a volume weighted median particle diameter well above 20 microns, usually the particles weighted by volume have a particle diameter well in excess of 100 microns. The dry TS-1 particles optionally admixed with binder are passed via an air carrier through a ceramic jet mill with narrow plate spacing with recycle of solid as necessary until the weighted by volume average particle diameter is reduced to less than 5 microns in size. This is checked using a Malvern particle size analyzer or equivalent or scanning electron microscopy.

In a tank equipped with an agitator there is mixed 80 lb of water, 16 lb of the calcined, jet milled TS-1, and 4 lb of amorphous silica, the latter being high purity, colloidal silica having an average particle size of 5 nanometers. The resulting slurry is fed continuously through a variable speed pump and a transfer line to an 8 ft diameter Niro Atomizer Corporation spray dryer, through a stainless steel vaned atomizing wheel. The spray dryer consists of an upper cylindrical section and a lower conical section, which is contiguous with the cylindrical portion. Air, preheated to 800° F. (427° C.) using natural gas (methane) combustion is fed to the top of the spray dryer. The spray dried particles are collected via a rotary star discharge valve, into a container at the base of the conical section of the dryer, the mouth of the container being clamped to the bottom flange of the rotary discharge valve. The spent heating air exits the side of the conical section of the dryer and exhausts to the ambient air via a water scrubber, bag filters and a second fan, which maintains the air flow through the bag house. The spray dried product has a median diameter of 40 microns, weighted by volume, and a median size of 25 microns diameter, weighted by number. There is little or no product less than 10 microns in diameter. The particles are porous spheres, with a minor proportion having dimples or hollows. Cracks and other imperfections in the morphology are rare, as determined by scanning electron microscopy. The theoretical spray dried TS-1 composition, after complete drying is 80 wt % TS-1, and 20 wt % amorphous silica.

Pd is then applied to the spray dried material in order to form a catalyst for propylene oxide production. The spray dried TS-1 composition is dried at 110° C. and calcined at 550° C. in an oxygen-containing atmosphere. 70 gm of the dried and calcined spray dried TS-1 composition is mixed with a solution of 0.259 gm of palladium tetraamine dichloride monohydrate in 250 gm of deionized water with application of minimal mechanical agitation. The mixture is heated to 30° C. and soaked for 16 hours to conduct the Pd ion exchange. The mixture is then filtered to separate solid from liquid using a nominal 10 micron filter. The filtered solids are washed three times with deionized water, and dried in an oven at 50° C. under vacuum and heated to 110° C. where it is maintained for 2 hours. The dried product is calcined by ramping the temperature at 2° C./min to 300° C. where it is held for 4 hours. The solids are cooled and flushed with nitrogen gas. The catalyst is reduced by contact with 4% hydrogen in nitrogen at 50° C. for 4 hours. The equipment is flushed with nitrogen to eliminate the hydrogen. The theoretical Pd is 0.149 wt %, the experimental Pd on finished catalyst is 0.10 wt %.

As a result of the particle size reduction prior to spray drying, the activity of the TS-1 after spray drying is substantially increased. In addition, the epoxidation activity of the spray dried catalyst is higher than predicted. The volume-specific production rate of propylene oxide is increased which increases production rate relative to the cost of equipment.

The catalyst thus prepared is used to catalyze the production of propylene oxide in accordance with known procedures. Illustratively, a slurry is formed comprised of 10 wt % of the finished in situ catalyst which is described above. Hydrogen, oxygen and propylene in molar ratio of about 2 to 1 to 1.3 are fed to the slurry and reacted at about 65° C. under 850 psig pressure to form propylene oxide. The reaction mixture is worked up to recover product propylene oxide according to known procedures.

The above experimental procedure can be varied in a number of ways, including, changing the proportion of Ti in the TS-1 preparation by varying the amount of Ti compound; varying relative amount of TPAOH used; application of the Pd to the TS-1, if already calcined, before spray drying; spray drying the TS-1 with the tetrapropylammonium hydroxide template left in with the spray dried product calcined afterwards to remove template; use of other binders, such as amorphous alumina and mixtures of amorphous alumina and silica can be used; application of additional catalyst components such as gold which can be added after the palladium; other materials such as zinc nitrate and zinc oxide can be spray dried with the TS-1, in which case calcination resolves the zinc as zinc oxide.

We claim:

1. In a process for the preparation of TS-1 catalyst particles suitable for the production of oxirane compounds from TS-1 particles having a median diameter weighted by volume of 10 microns or higher, the improvement of reducing the average diameter of the TS-1 particles weighted by volume, to below 10 microns and spray drying an aqueous suspension of the size reduced TS-1 particles.

2. The process for producing an oxirane compound which comprises epoxidizing an olefin by catalytic reaction with hydrogen peroxide wherein the catalyst is produced by the process of claim 1.

3. The process for producing an oxirane compound which comprises reacting an olefin, hydrogen and oxygen at epoxidizing conditions in the presence of a catalyst comprised of a noble metal supported on TS-1 produced by the process of claim 1.

4. The process of claim 1 wherein the catalyst particles are also comprised of binder.

5. The process of claim 2 wherein the olefin is propylene.

6. The process of claim 3 wherein the olefin is propylene.

7. The process of claim 3 wherein the noble metal is palladium.

8. The process of claim 1 wherein the average diameter of the TS-1 particles weighted by volume is reduced to less than 5 microns.

* * * * *